United States Patent
Perez, III

(10) Patent No.: US 9,913,640 B2
(45) Date of Patent: Mar. 13, 2018

(54) SUTURE TENSIONING DEVICE

(71) Applicant: Arthrex, Inc., Naples, FL (US)

(72) Inventor: Arley Perez, III, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 938 days.

(21) Appl. No.: 14/091,400

(22) Filed: Nov. 27, 2013

(65) Prior Publication Data

US 2014/0276990 A1 Sep. 18, 2014

Related U.S. Application Data

(60) Provisional application No. 61/778,717, filed on Mar. 13, 2013.

(51) Int. Cl.
*A61B 17/04* (2006.01)

(52) U.S. Cl.
CPC .. *A61B 17/0483* (2013.01); *A61B 2017/0496* (2013.01)

(58) Field of Classification Search
CPC ............... A61B 2017/0496; A61B 17/0483
See application file for complete search history.

(56) References Cited

U.S. PATENT DOCUMENTS

| | | |
|---|---|---|
| 4,823,794 A | 4/1989 | Pierce |
| 8,123,806 B1 | 2/2012 | Hoof |
| 2004/0102809 A1* | 5/2004 | Anderson .......... A61B 17/0487 606/232 |
| 2005/0131430 A1 | 6/2005 | Ravikumar |
| 2007/0021781 A1 | 1/2007 | Jervis et al. |
| 2008/0275477 A1 | 11/2008 | Sterrett et al. |
| 2009/0248028 A1* | 10/2009 | Alexander ......... A61B 17/0487 606/103 |
| 2010/0001038 A1 | 1/2010 | Levin et al. |
| 2010/0305571 A1 | 12/2010 | Pratt et al. |

FOREIGN PATENT DOCUMENTS

WO 95/32669 A1 12/1995

OTHER PUBLICATIONS

International Preliminary Report on Patentability for International Application No. PCT/US2014/021045 dated Sep. 24, 2015.
International Search Report & Written Opinion for International Application No. PCT/US2014/021045 dated Oct. 23, 2014.
Invitation to Pay Additional Fees and, Where Applicable, Protest Fee for International Application No. PCT/US2014/021045 dated May 25, 2014.

* cited by examiner

*Primary Examiner* — Richard Louis
(74) *Attorney, Agent, or Firm* — Carlson, Gaskey & Olds, P.C.

(57) ABSTRACT

A suture tensioning device includes a first portion including a first inner surface having a first surface and a first beveled surface and another first portion including another first inner surface having another first surface and another first beveled surface. The first surface of the first inner surface and the another first surface of the another first inner surface contact. The first portion and the another first portion are connected to define a first handle. A first cleat is defined between the first beveled surface and the another first beveled surface.

19 Claims, 5 Drawing Sheets

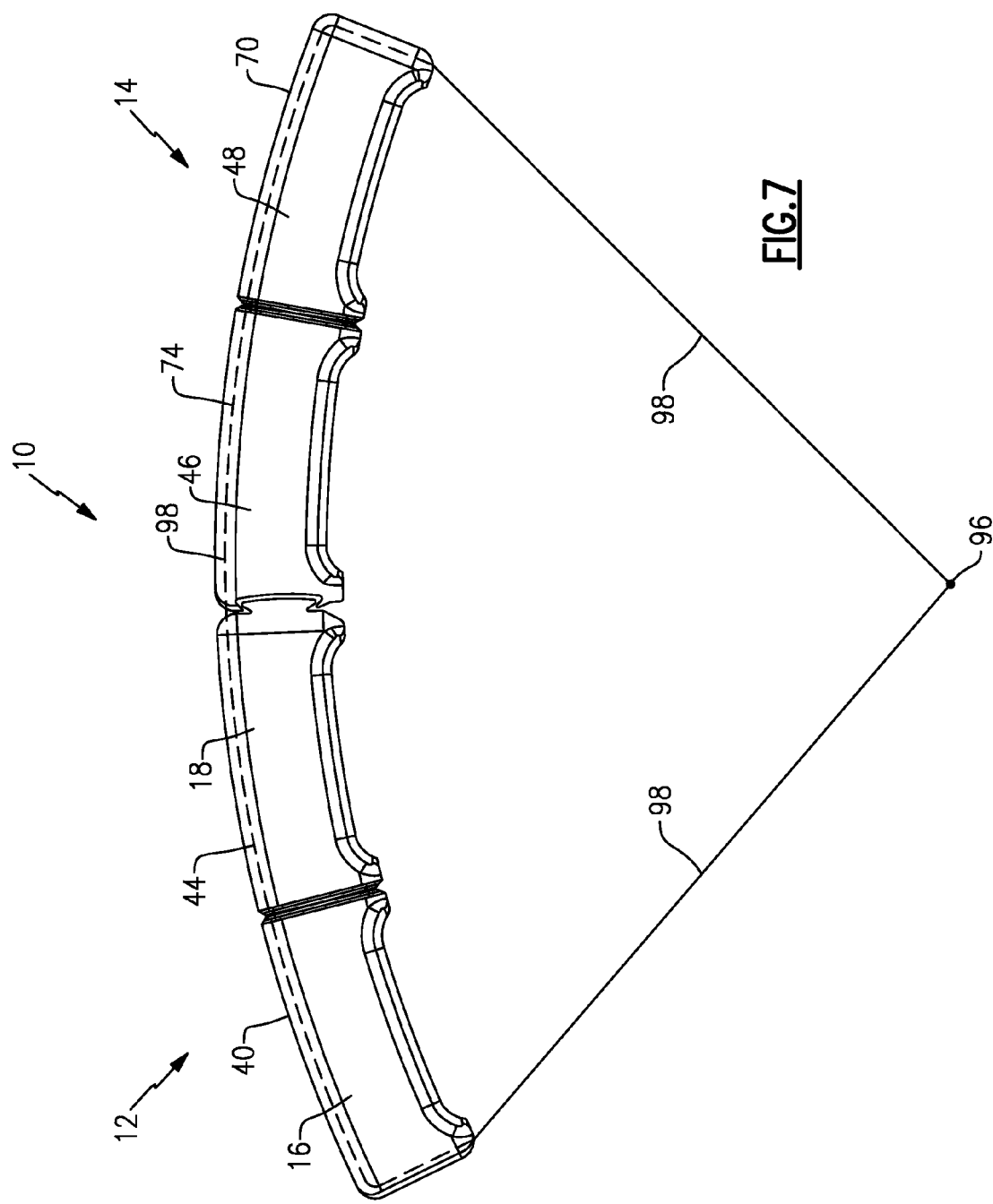

SUTURE TENSIONING DEVICE

REFERENCE TO RELATED APPLICATIONS

This application claims priority to U.S. Provisional Patent Application No. 61/778,717 filed Mar. 13, 2013.

BACKGROUND OF THE INVENTION

A suture tensioning device can be employed to tension a suture during a surgical procedure, such as a tissue fixation procedure that repairs or replaces a tendon or ligament with a graft to bone. A suture tensioning device provides additional leverage to tighten the suture without damaging the suture, the bone or the tissue. A previous suture tensioning device includes a cannulated tube, and a suture is fed through at least a portion of the cannulated tube.

SUMMARY OF THE INVENTION

A suture tensioning device includes a first portion including a first inner surface having a first surface and a first beveled surface and another first portion including another first inner surface having another first surface and another first beveled surface. The first surface of the first inner surface and the another first surface of the another first inner surface contact. The first portion and the another first portion are connected to define a first handle. A first cleat is defined between the first beveled surface and the another first beveled surface.

A suture tensioning device includes a first handle including a first portion having a first inner surface with a first surface and a first beveled surface and another first portion having another first inner surface having another first surface and another first beveled surface. The first portion of the first inner surface and the another first portion of the another first inner surface contact. The first portion and the another first portion are connected to define a first handle. A first cleat is defined between the first beveled surface and the another first beveled surface, and the first handle includes one of a projection and a recess. The suture tensioning device includes a second handle including a second portion having a second inner surface with a second surface and a second beveled surface and another second portion having another second inner surface having another second surface and another second beveled surface. The second portion of the second inner surface and the another second portion of the another second inner surface contact. The second portion and the another second portion are connected to define a second handle. A second cleat is defined between the second beveled portion and the another second beveled portion, and the second handle includes the other of the projection and the recess. The projection is received in the recess to removably attach the first handle to the second handle.

These and other features of the present invention can be best understood from the following specification and drawings, the following of which is a brief description.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows:

FIG. 7 illustrates a second example of tensioning a suture with the suture tensioning device.

DETAILED DESCRIPTION OF THE PREFERRED EMBODIMENTS

Figure 1:
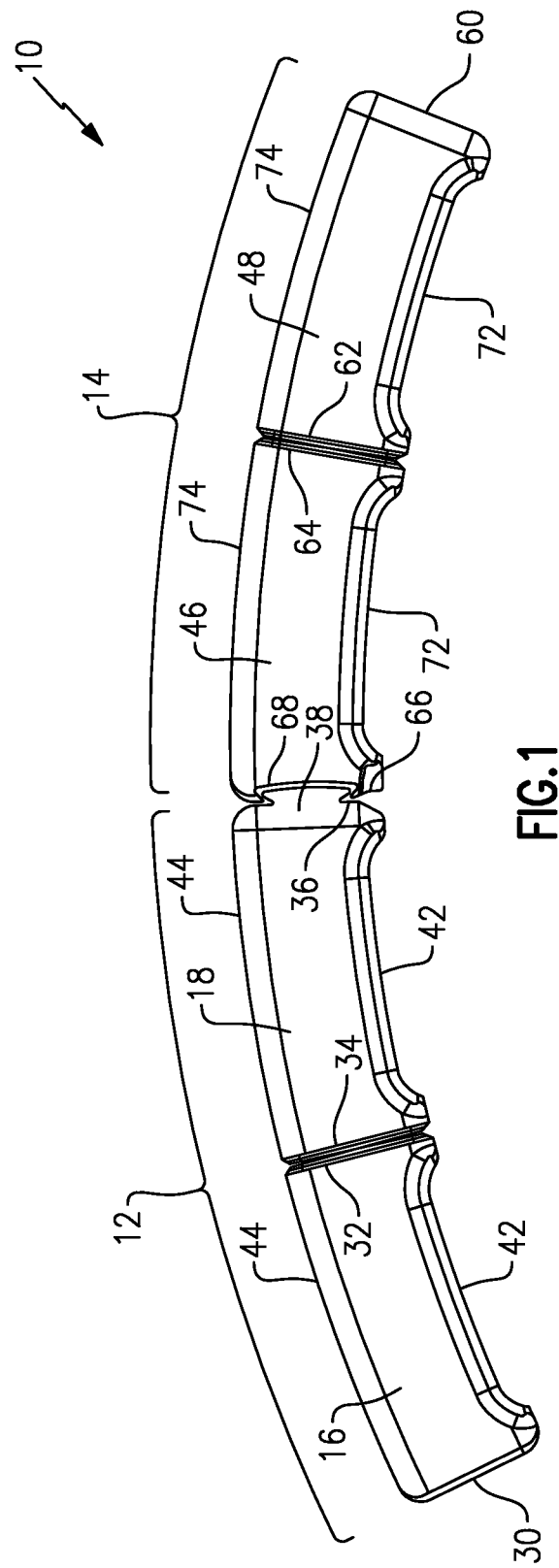
FIG. 1 illustrates a side view of a suture tensioning device.

FIG. 1 illustrates a suture tensioning device 10 employed to tension two sutures tails 94 or sutures 98 (shown in FIGS. 6 and 7, respectively) during a surgical procedure. The suture tensioning device 10 includes a first handle 12 and a second handle 14 that can be connected together or used individually by disconnecting the first handle 12 and the second handle 14. In one example, the first handle 12 and the second handle 14 of the suture tensioning device 10 are made of plastic. Each of the first handle 12 and the second handle 14 have a slightly arcuate shape, and the suture tensioning device 10 has an arcuate shape when the first handle 12 and the second handle 14 are attached together.

Figure 2:
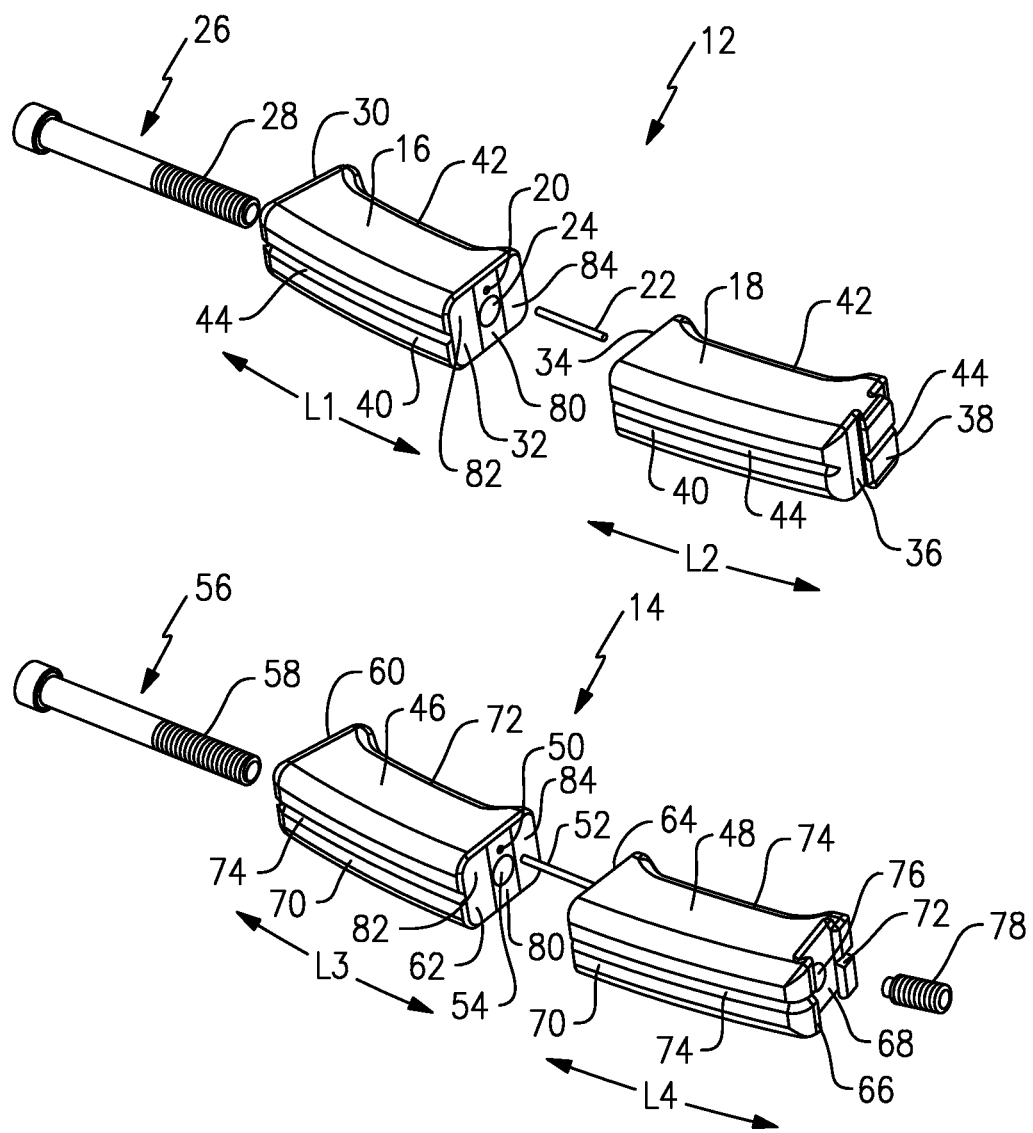
FIG. 2 illustrates an exploded view of a first handle and a second handle of the suture tensioning device.

As shown in FIG. 2, the first handle 12 includes a first portion 16 and a second portion 18. The first portion 16 and the second portion 18 each includes a bore (the first portion 16 includes a bore 20 as shown in FIG. 2) that align to receive an alignment feature 22 that aligns the first portion 16 and the second portion 18 relative to each other. In one example, the alignment feature 22 is a pin.

The first portion 16 includes a bore 24 that extends through a length L1 of the first portion 16, and the second portion 18 includes a bore (not shown) and that extends partially through a length L2 of the second portion 18 and aligns with the bore 24 of the first portion 16. A fastener 26 is received in the aligned bores 24 to secure the first portion 16 and the second portion 18 together. In one example, the fastener 26 is a threaded fastener 28.

The first portion 16 includes an outer side surface 30 and an opposing inner side surface 32. The bore 24 extends between the side surfaces 30 and 32. The second portion 18 includes an inner side surface 34 and an outer side surface 36. The bore (not shown) of the second portion 18 extends from the inner side surface 34 of the second portion 18 and partially through the length L2 of the second portion 18. The fastener 26 is inserted into the bore 24 from the outer side surface 30 of the first portion 16 and then enters into the bore (not shown) of the second portion 18. When attached, a portion of the inner side surface 32 of the first portion 16 contacts a portion of the inner side surface 34 of the second portion 18. The outer side surface 36 of the second portion 18 includes a locking projection 38.

Each of the first portion 16 and the second portion 18 of the first handle 12 includes an upper curved surface 40 and a lower curved surface 42. A groove 44 is located on the outer side surfaces 30 and 36 and the upper curved surface 40.

Figure 3:
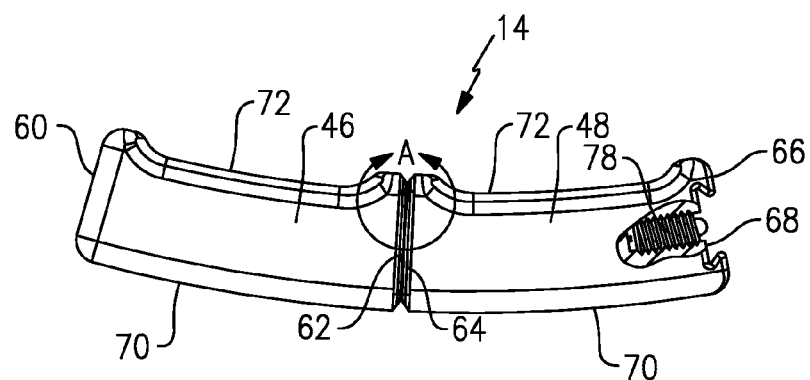
FIG. 3 illustrates a side view of the second handle of the suture tensioning device.
Figure 4:
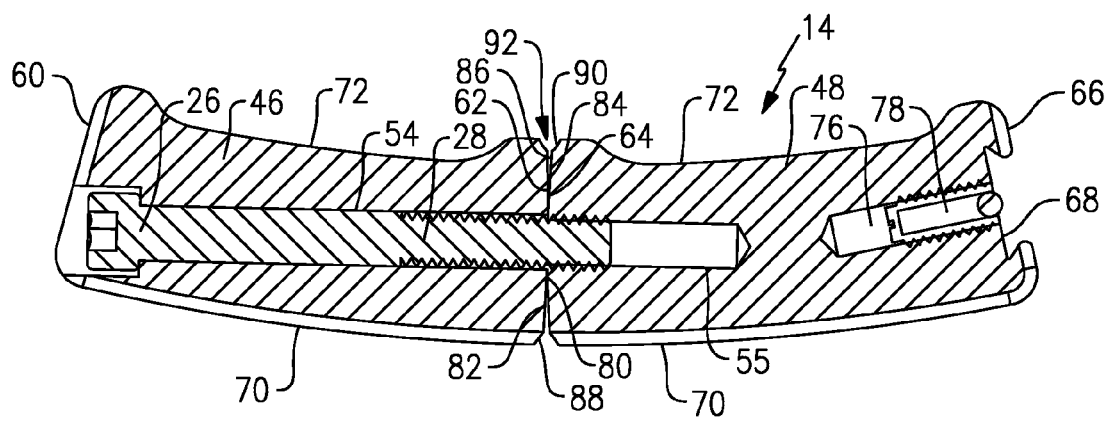
FIG. 4 illustrates a cross-sectional side view of the second handle of the suture tensioning device.

As further shown in FIGS. 3 and 4, the second handle 14 includes a first portion 46 and a second portion 48. The first portion 46 and the second portion 48 each include a bore (FIG. 2 shows the bore 50 of the first portion 46) that align to receive an alignment feature 52 that aligns the first portion 46 and the second portion 48 relative to each other. In one example, the alignment feature 52 is a pin.

The first portion 46 includes a bore 54 that extends through a length L3 of the first portion 46, and the second portion 48 includes a bore 55 that extends partially through a length L4 of the second portion 48. When aligned, a fastener 56 is received in the aligned bores 54 and 55 to secure the first portion 46 and the second portion 48 together. In one example, the fastener 56 is a threaded fastener 58.

The first portion 46 includes an outer side surface 60 and an opposing inner side surface 62, and the bore 54 extends between the side surfaces 60 and 62. The second portion 48 includes an inner side surface 64 and an outer side surface 66, and the bore 55 extends from the inner side surface 64 of the second portion 48. The fastener 56 is inserted into the bore 54 from the outer side surface 60 of the first portion 46. When attached, a portion of the inner side surface 62 of the first portion 46 contacts a portion of the inner side surface 64 of the second portion 48.

Each of the first portion 46 and the second portion 48 of the first handle 12 also includes an upper curved surface 70 and a lower curved surface 72. A groove 74 is located on the outer side surfaces 60 and 66 and the upper curved surface 70.

The outer side surface 66 of the second portion 48 includes a recess 68. Returning to FIG. 1, the locking projection 38 of the first handle 12 is received in the recess 68 of the second handle 14 to remotely attach the first handle 12 to the second handle 14 and define the suture tensioning device 10.

A bore 76 extends from the outer side surface 66 of the second handle 14 and partially through the length L4 of the second portion 48. A plunger 78 received in the bore 76 is resiliently biased outwardly to provide tactile feedback when the locking projection 38 of the first handle 12 is received in the recess 68 of the second handle 14, allowing the handles 12 and 14 to be easily connected and detached from each other.

Although FIGS. 3 and 4 illustrate the second handle 14 of the suture tensioning device 10, the first handle 12 includes similar features and structures, except the first handle 12 does not include the recess 68, the bore 76 and the plunger 78, and the first handle 12 does include the locking projection 38.

Each of the inner side surfaces 32 and 34 of the first handle 12 and the inner side surfaces 62 and 64 of the second handle 14 include a flattened surface 80, an upper beveled surface 82 and a lower beveled surface 84. The flattened surfaces 80 of the first handle 12 contact when the first portion 16 and the second portion 18 of the first handle 12 are secured together with the fastener 26, and the flattened surfaces 80 of the second handle 14 contact when the first portion 46 and the second portion 48 of the second handle 14 are secured together with the fastener 56. This allows the first handle 12 and the second handle 14 to be used individually and separately.

Figure 5:
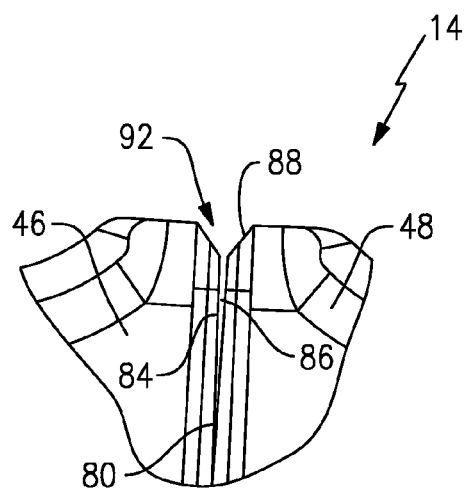
FIG. 5 illustrates a cleat and a groove of the second handle of the suture tensioning device.

As shown in FIG. 4, when the first portion 46 and the second portion 48 of the second handle 14 are attached, a cleat 86 is defined between each of the upper beveled surfaces 82 and also between each of the lower beveled surfaces 84. FIG. 5 illustrates an area A of FIG. 4 showing the cleat 86 of the second handle 14. Additionally, when the first portion 16 and the second portion 18 of the first handle 12 are attached, a cleat (not shown) is defined between each of the upper beveled surfaces 82 and also between each of the lower beveled surfaces 84.

Another upper beveled surface 88 is located outwardly of each of the upper beveled surfaces 82, and another lower beveled surface 90 is located outwardly of each of the lower beveled surfaces 84. When the first portion 16 and the second portion 18 of the first handle 12 are connected and the first portion 46 and the second portions 48 of the second handle 14 are connected, a groove 92 is defined between the adjacent upper beveled surfaces 88 and also between the adjacent lower beveled surfaces 90. In one example, the grooves 92 are v-shaped.

The suture tensioning device 10 is employed to tension two suture tails 94 that are connected at a common area 96 during a surgical procedure. In one example, the suture tensioning device 10 can be Tightrope®, a registered trademark of Arthrex, Inc. of Naples, Fla.

Figure 6:
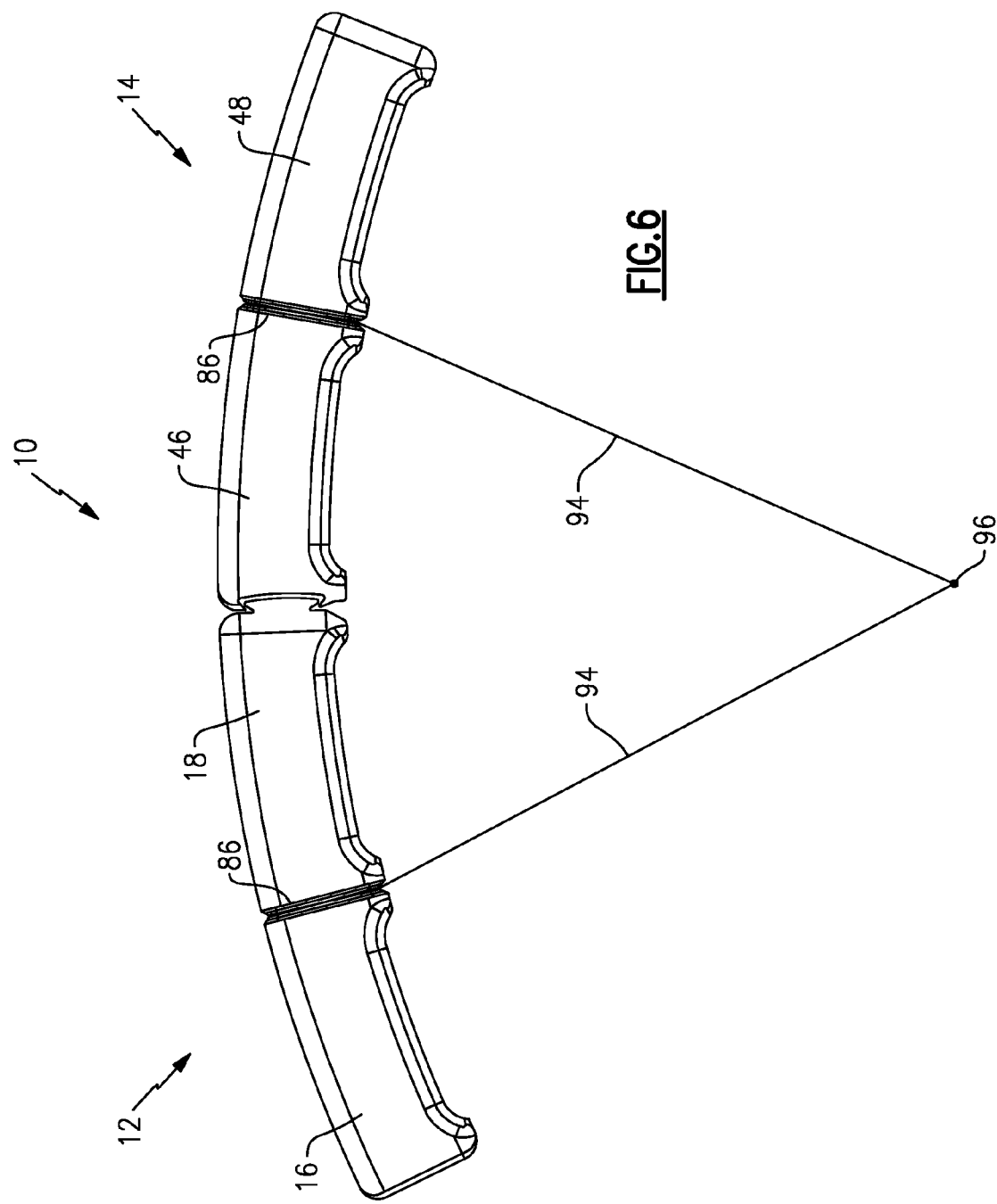
FIG. 6 illustrates a first example of tensioning a suture with the suture tensioning device.

As shown in FIG. 6, in one example, one suture tail 94 is wedged in the cleat 86 of each of the handles 12 and 14 of the suture tensioning device 10, securing the suture tails 94 to the suture tensioning device 10 during a surgical procedure. This allows the suture tensioning device 10 to firmly, securely, and atraumatically secure the suture tails 94 in a quick and simple manner, allowing a surgeon or other medical professional to tension the suture tails 94 as needed during a surgical procedure. The cleat 86 both retains the suture tails 94 and guides the suture tails 94 between the two handles 12 and 14. The handles 12 and 14 can be connected as shown in FIG. 6, or the handles 12 and 14 can be separated such that one handle 12 and 14 is held in each hand.

In another example, each of the suture tails 94 are received in one of the grooves 92, and the suture tails 94 are wrapped around the handles 12 and 14. The handles 12 and 14 can be connected as shown in FIG. 6, or the handles 12 and 14 can be separated such that one handle 12 and 14 is held in each hand.

In another example shown in FIG. 7, a single suture 98 is received in the grooves 44 and 74 (the suture 98 is partially shown in dotted lines in FIG. 7 when received in the grooves 44 and 74) located on the outer side surfaces 30 and 60, respectively, and the upper curved surfaces 40 and 70, respectively, of the first handle 12 and the second handle 14, respectively, of the suture tensioning device 10. Portions of the single suture 98 also meet in the common area 96. The handles 12 and 14 can be connected as shown in FIG. 7, or separated such that one handle 12 and 14 is held in each hand.

Minimal suture wraps are needed to secure the suture tails 94 or the suture 98 to the suture tensioning device 10, simplifying use. Although a suture tail 94 or a suture 98 has been illustrated and described, wire, tape, or any time of material that needs to be tensioned during a surgical procedure can be employed.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A suture tensioning device comprising:
a first handle including a first portion and another first portion connected to the first portion, wherein the first portion includes a first inner surface having a first surface and a first beveled surface, the another first portion includes another first inner surface having another first surface and another first beveled surface, wherein the first surface of the first inner surface and the another first surface of the another first inner surface contact, a first cleat is defined between the first beveled surface and the another first beveled surface, and the first portion and the another first portion both have an arcuate shape,
wherein the first handle includes a first outer surface having a first groove and another first outer surface having another first groove, wherein the first outer surface and the another first outer surface are in different planes, and a suture is receivable in the first groove and the another first groove to tension the suture.

2. The suture tensioning device as recited in claim 1 wherein a threaded fastener secures the first portion and the another first portion together.

3. The suture tensioning device as recited in claim 1 wherein the first inner surface of the first portion includes an additional first beveled surface and the another first inner surface of the another first portion includes an additional another first beveled surface, the first surface is located between the first beveled surface and the additional first beveled surface, the another first surface is located between the another first beveled surface and the additional another first beveled surface, and another first cleat is defined between the additional first beveled surface and the additional another first beveled surface.

4. The suture tensioning device as recited in claim 3 wherein the first groove is outwardly of the first cleat and the another first groove is outwardly of the another first cleat.

5. The suture tensioning device as recited in claim 4 wherein the first groove and the another first groove are each substantially v-shaped.

6. The suture tensioning device as recited in claim 1 including a second handle having a second portion having a second inner surface with a second surface and a second beveled surface, another second portion including another second inner surface having another second surface and another second beveled surface, wherein the second surface of the second inner surface and the another second surface of the another second inner surface contact, and the second portion and the another second portion are connected to define the second handle, and a second cleat is defined between the second beveled surface and the another second beveled surface.

7. The suture tensioning device as recited in claim 1 including a second handle attached to the first handle.

8. The suture tensioning device as recited in claim 7 wherein the first handle includes one of a projection and a recess and the second handle includes the other of the projection and the recess, and the projection is received in the recess to attach the first handle to the second handle to removably attach the first handle to the second handle.

9. The suture tensioning device as recited in claim 1 wherein the first portion and the another first portion have substantially the same shape.

10. The suture tensioning device as recited in claim 1 wherein the first groove is continuous with the second groove to define a single groove.

11. The suture tensioning device as recited in claim 1 wherein the first upper surface and the opposing outer side surfaces define an outer perimeter of the first handle.

12. A suture tensioning device comprising:
a first handle including a first portion and another first portion connected to the first portion, wherein the first portion includes a first inner surface having a first surface and a first beveled surface, the another first portion includes another first inner surface having another first surface and another first beveled surface, wherein the first surface of the first inner surface and the another first surface of the another first inner surface contact, wherein the first handle includes one of a projection and a recess and a second handle includes the other of the projection and the recess, and the projection is received in the recess to attach the first handle to the second handle to removably attach the first handle to the second handle, and a first cleat is defined between the first beveled surface and the another first beveled surface; and
the second handle including a second portion having a second inner surface with a second surface and a second beveled surface, another second portion including another second inner surface having another second surface and another second beveled surface, wherein the second surface of the second inner surface and the another second surface of the another second inner surface contact, and the second portion and the another second portion are connected to define the second handle, and a second cleat is defined between the second beveled surface and the another second beveled surface.

13. The suture tensioning device as recited in claim 12 wherein the recess includes a bore, and a plunger is received in the bore and is biased towards the projection to provide tactile feedback when the projection of the first handle is received in the recess.

14. A suture tensioning device comprising:
a first handle including a first portion having a first inner surface with a first surface and a first beveled surface, another first portion having another first inner surface having another first surface and another first beveled surface, wherein the first portion of the first inner surface and the another first portion of the another first inner surface contact, the first portion and the another first portion are connected to define a first handle, a first cleat is defined between the first beveled surface and the another first beveled surface, and the first handle includes one of a projection and a recess; and
a second handle including a second portion having a second inner surface with a second surface and a second beveled surface, another second portion having another second inner surface having another second surface and another second beveled surface, wherein the second portion of the second inner surface and the another second portion of the another second inner surface contact, the second portion and the another second portion are connected to define a second handle, a second cleat is defined between the second beveled portion and the another second beveled portion, and the second handle includes the other of the projection and the recess,
wherein the projection is received in the recess to removably attach the first handle to the second handle.

15. The suture tensioning device as recited in claim 14 wherein the first handle and the second handle each have an arcuate shape.

16. The suture tension device as recited in claim 14 wherein the recess includes a bore, and a plunger is received in the bore and is biased towards the projection to provide tactile feedback when the projection is received in the recess.

17. The suture tensioning device as recited in claim 14 wherein a suture is located in the first cleat and the second cleat.

18. The suture tensioning device as recited in claim 14 including a groove on an upper surface and an outer side surface of each of the first handle and the second handle, and a suture is received in the groove.

19. A suture tensioning device comprising:
a first handle including a first portion and another first portion connected to the first portion, wherein the first portion includes a first inner surface having a first surface and a first beveled surface, the another first portion includes another first inner surface having another first surface and another first beveled surface, wherein the first surface of the first inner surface and the another first surface of the another first inner surface contact; and
a second handle, wherein the first handle includes one of a projection and a recess and the second handle includes the other of the projection and the recess, and the projection is received in the recess to removably attach the first handle to the second handle.

\* \* \* \* \*